(12) United States Patent
Shelton, IV et al.

(10) Patent No.: US 10,080,622 B2
(45) Date of Patent: Sep. 25, 2018

(54) ROBOTICS TOOL BAILOUTS

(71) Applicant: Ethicon Endo-Surgery, LLC, Guaynabo, PR (US)

(72) Inventors: Frederick E. Shelton, IV, Hillsboro, OH (US); Jason L. Harris, Lebanon, OH (US); Jeffrey S. Swayze, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 219 days.

(21) Appl. No.: 15/237,886

(22) Filed: Aug. 16, 2016

(65) Prior Publication Data

US 2018/0049836 A1    Feb. 22, 2018

(51) Int. Cl.
| | |
|---|---|
| *F16H 37/06* | (2006.01) |
| *A61B 90/00* | (2016.01) |
| *A61B 34/30* | (2016.01) |
| *A61B 17/00* | (2006.01) |

(52) U.S. Cl.
CPC ........ *A61B 90/03* (2016.02); *A61B 17/00234* (2013.01); *A61B 34/30* (2016.02); *A61B 2017/00221* (2013.01); *A61B 2017/00398* (2013.01); *A61B 2090/031* (2016.02); *A61B 2090/033* (2016.02)

(58) Field of Classification Search
CPC ... A61B 90/03; A61B 34/30; A61B 17/00234; A61B 2090/033; A61B 2017/00398; A61B 2017/00221; A61B 2090/031; F16H 37/065

USPC ........................................................ 74/665 L
See application file for complete search history.

(56) References Cited

U.S. PATENT DOCUMENTS

| | | | | |
|---|---|---|---|---|
| 4,848,338 | A * | 7/1989 | De Satnick | A61B 17/29 606/1 |
| 5,433,725 | A * | 7/1995 | Christian | A61B 17/29 600/104 |
| 5,676,678 | A * | 10/1997 | Schad | A61B 17/29 606/170 |
| 8,114,345 | B2 | 2/2012 | Dlugos, Jr. et al. | |
| 8,882,792 | B2 | 11/2014 | Dietz et al. | |
| 8,915,842 | B2 | 12/2014 | Weisenburgh, II et al. | |
| 8,931,682 | B2 | 1/2015 | Timm et al. | |
| 8,945,098 | B2 | 2/2015 | Seibold et al. | |
| 2001/0031983 | A1* | 10/2001 | Brock | A61B 34/71 606/205 |

(Continued)

OTHER PUBLICATIONS

Correlated Solutions, "Principle of Digital Image Correlation," 2013 (http://correlatedsolutions.com/digital-image-correlation/).

(Continued)

*Primary Examiner* — Ha Dinh Ho
(74) *Attorney, Agent, or Firm* — Mintz Levin Cohn Ferris Glovsky and Popeo, P.C.

(57) ABSTRACT

Methods and devices are provided for robotic surgery, and in particular for retracting and/or bailing out robotic tools. For example, surgical tools, methods, and systems are provided having bailout assemblies for selectively bailing out one or more functions of an end effector of a surgical tool. Surgical tools, methods, and systems are also provided with bailout assemblies for simultaneously bailing out a plurality of functions of an end effector of a surgical tool.

19 Claims, 12 Drawing Sheets

(56) References Cited

U.S. PATENT DOCUMENTS

| | | | |
|---|---|---|---|
| 2008/0021278 A1* | 1/2008 | Leonard | A61B 17/1608 |
| | | | 600/129 |
| 2008/0081948 A1 | 4/2008 | Weisenburgh et al. | |
| 2011/0118709 A1 | 5/2011 | Burbank | |
| 2011/0118778 A1 | 5/2011 | Burbank | |
| 2013/0282052 A1 | 10/2013 | Aranyi et al. | |
| 2014/0005718 A1 | 1/2014 | Shelton, IV et al. | |

OTHER PUBLICATIONS

U.S. Appl. No. 15/131,963 entitled "Method for Operating a Surgical Instrument" filed Apr. 18, 2016.
U.S. Appl. No. 15/177,430 entitled "Surgical Instrument With User Adaptable Techniques" filed Jun. 9, 2016.

* cited by examiner

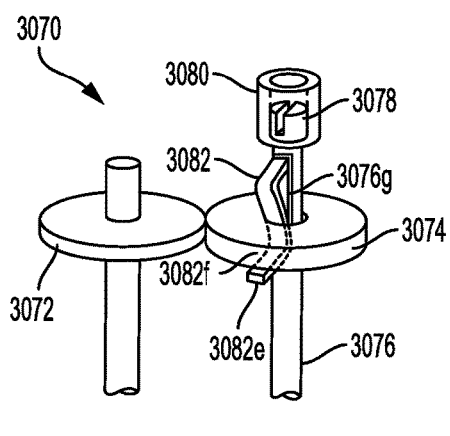
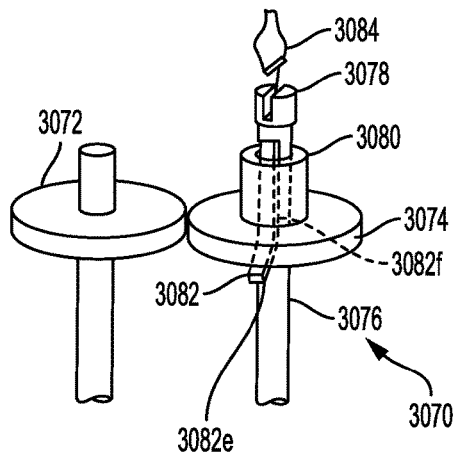
FIG. 13  FIG. 14
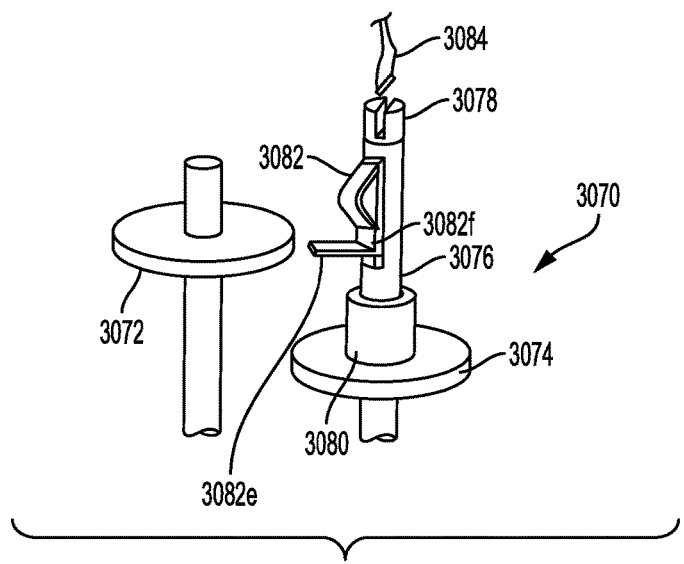
FIG. 15

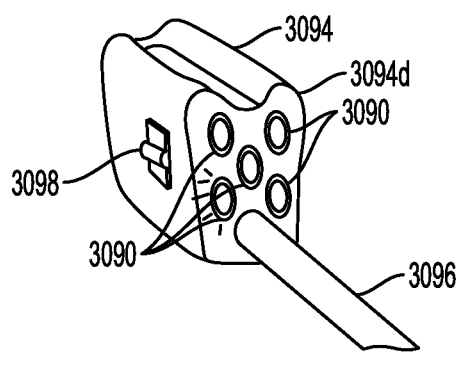 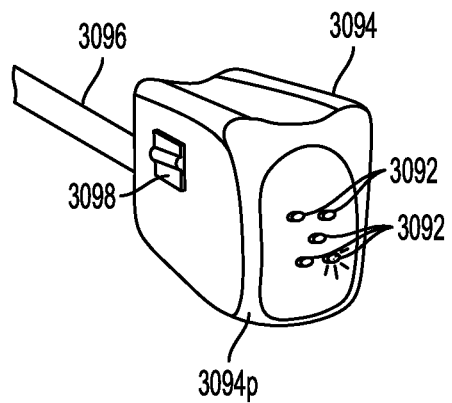
FIG. 16  FIG. 17
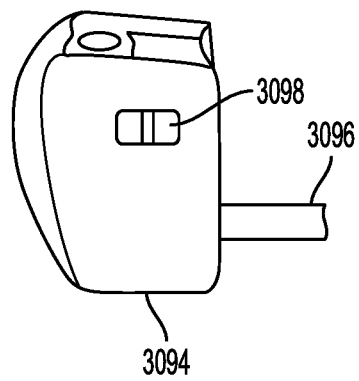
FIG. 18

ROBOTICS TOOL BAILOUTS

FIELD OF THE INVENTION

Methods and devices are provided for robotic surgery, and in particular for retracting and/or bailing out robotic tools.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, the relative remoteness of the instruments makes responding to any emergencies and/or errors during the surgery difficult. For example, if one or more instruments malfunction, it can be desirable to rapidly release any tissue coupled to the instruments and retract the instruments. But the remote placement of the instruments and the minimally-invasive nature of the surgery may make this desire difficult.

Thus it can be desirable to allow rapid release, reversal, and/or retraction of surgical instruments within a patient even if the instruments experience errors, malfunctions, and/or failures. While significant advances have been made in the field of robotic surgery, there remains a need for improved methods, systems, and devices for use in robotic surgery.

SUMMARY OF THE INVENTION

Various surgical tools and methods are provided having bailout assemblies for selectively bailing out one or more functions of the end effector of the surgical tool. In one embodiment, a surgical tool is provided and includes a housing having a plurality of motor-driven drive gears, and an elongate shaft extending distally from the housing. An end effector is coupled to a distal end of the elongate shaft. The device also includes a plurality of actuation assemblies. Each actuation assembly can be coupled to one of the plurality of motor-driven drive gears such that each of the motor-driven drive gears is configured to drive a corresponding actuation assembly. Each actuation assembly can also configured to operate a function of the end effector. The device can further include a plurality of bailout mechanisms, with each bailout mechanism being selectively engageable with one of the plurality of actuation assemblies for manually driving the actuation assembly.

In one embodiment, each bailout mechanism can include a one-way gear configured to selectively engage the actuation assembly and configured to be rotatable in only one direction to drive the actuation assembly in a reverse direction. The one-way gear can be accessible from an exterior of the housing and it can be configured to move into engagement with the actuation assembly. The device can also include a rotatable lever coupled to the one-way gear such that rotation of the lever is effective to cause corresponding rotation of the one-way gear.

In other aspects, each actuation assembly can be movable from a first position in which the actuation assembly is engaged with the corresponding motor-driven drive gear, to a second position in which the actuation assembly is disengaged with the corresponding motor-driven drive gear. Each actuation assembly can be configured such that it is prevented from moving from the second position to the first position. In one embodiment, each actuation assembly can include a gear mounted on a shaft, the gear being engaged with the corresponding motor-driven drive gear in the first position, and the gear moving away from and out of engagement with the motor-driven drive gear in the second position. In one embodiment, the shaft can be configured to move with the gear when the gear is moved away from and out of engagement with the motor-driven drive gear, and the shaft can include tabs that engage the housing to prevent movement of the shaft, thereby locking the actuation assembly in the second position. In other aspects, the gear mounted on the shaft of each actuation assembly can be held in engagement with the corresponding motor-driven drive gear by a spring, and a collar can be disposed on the shaft and is configured to advance over the spring to release the gear thereby allowing the gear to move out of engagement with the motor-driven drive gear.

In other embodiments, the tool can include a decoupling assembly coupled to first and second actuation assemblies of the plurality of actuation assemblies. The decoupling assembly can be configured to simultaneously cause a first gear of the first actuation assembly and a second gear of the second actuation assembly to move out of engagement with the corresponding motor-driven drive gears. The first actuation assembly can be effective to close opposed jaws of the end effector, and the second actuation assembly can be effective to first a plurality of staples from the end effector. In certain aspects, the decoupling assembly can include a threaded shaft and a housing threadably mounted on the threaded shaft. The housing can have first and second pusher rods mated thereto and mated to the first and second gears such that rotation of the threaded shaft causes translation of the housing such that the first and second pusher rods push the first and second gears away from the corresponding motor-driven drive gears.

In another embodiment, each bailout mechanism can include an indicator configured to indicate when the actuation assembly coupled thereto has failed. The bailout mechanisms can include other features such as torque limiters as well.

Surgical bailout methods are also provided and in one embodiment, the method includes selectively actuating a plurality of motors in a tool driver of a robotic arm to selectively drive a plurality of drive gears disposed within a housing of a surgical tool. Each of the plurality of drive gears can drive an actuation assembly extending through an elongate shaft of the surgical tool to thereby actuate a function of an end effector of the tool. The method can further include selectively moving a first bailout assembly of a plurality of bailout assemblies into engagement with a first actuation assembly of the plurality of actuation assemblies, and manually rotating the first bailout assembly to retract the first actuation assembly and thereby reverse the corresponding function of the end effector.

The method can also include decoupling the first actuation assembly from engagement with the corresponding drive gear. Decoupling the first actuation assembly can include releasing a spring biasing force applied to a gear of the first actuation assembly to allow the gear to move out of engagement with the corresponding drive gear. In other aspects, the method can include simultaneously decoupling the first actuation assembly and a second actuation assembly of the plurality of actuation assemblies from engagement with the corresponding drive gears. The method can also include moving the first actuation assembly from a first position, in which a gear of the first actuation assembly is positioned in engagement with a corresponding drive gear of the plurality of drive gears, to a second position, in which the gear of the first actuation assembly is spaced apart and disengaged from the corresponding drive gear of the plurality of drive gears. In other embodiments, the method can include selectively moving a second bailout assembly of a plurality of bailout assemblies into engagement with a second actuation assembly of the plurality of actuation assemblies, and manually rotating the second bailout assembly to retract the second actuation assembly and thereby reverse the corresponding function of the end effector.

Various surgical tools and methods are provided having bailout assemblies for simultaneously bailing out a plurality of functions of the end effector of the surgical tool. In one embodiment, a surgical tool is provided and includes a housing, an elongate shaft extending distally from the housing, and an end effector disposed at a distal end of the elongate shaft. The tool also include a plurality of actuation assemblies coupled to a plurality of motor-driven drive gears. Each of the motor-driven drive gears is configured to drive a corresponding actuation assembly, and each of the actuation assemblies is configured to operate a function of the end effector. The tool also includes a bailout mechanism configured to manually drive at least two of the plurality of actuation assemblies simultaneously to reverse the corresponding functions of the end effector.

In one embodiment, each motor-driven drive gear is selectively movable between a first position, in which the motor-driven drive gear has a coupling positioned to engage an external motor, and a second position, in which the coupling is positioned such that it is prevented from engaging an external motor. In other aspects, the bailout mechanism can include a crank arm configured to engage and drive the at least two actuation assemblies simultaneously.

In one embodiment, the bailout mechanism can include a bailout drive gear, and each of the plurality of actuation assemblies can include a gear that is selectively movable into engagement with the bailout drive gear such that rotation of the bailout drive gear can simultaneously drive at least two of the plurality of actuation assemblies. Each of the plurality of actuation assemblies can be coupled to a switch disposed on the housing and configured to move the gear of the actuation assembly into engagement with the bailout drive gear. Each switch can be configured to simultaneously move a corresponding motor-driven drive gear into a position in which the motor-driven drive gear is prevented from engaging with an external motor.

In other aspects, the bailout mechanism can be configured to be manually rotated to manually drive the at least two actuation assemblies. The bailout mechanism can include a drive recess configured to receive a drive tool. The drive tool can include a ratchet.

The tool can also include at least one indicator connected to at least one of the plurality of actuation assemblies and configured to indicate when the corresponding actuation assembly has failed. In other aspects, the housing can be configured to couple to a plurality of motors on a tool driver of a surgical system.

Bailout methods are also provided and in one embodiment the method includes selectively actuating a plurality of motors in a tool driver of a robotic arm to selectively drive a plurality of drive gears disposed within a housing of a surgical tool. Each of the plurality of drive gears drives an actuation assembly extending through an elongate shaft of the surgical tool to thereby actuate a function of an end effector of the tool. The method can further include actuating a bailout assembly to simultaneously counter rotate at least two of the plurality of actuation assemblies to reverse the corresponding functions of the end effector.

In one embodiment, the method further includes, prior to actuating the bailout assembly, decoupling the drive gears of the at least two of the plurality of actuation assemblies from the corresponding motors. Simultaneously with decoupling, the at least two of the plurality of actuation assemblies can move into engagement with the bailout assembly. In other aspects, decoupling the drive gears of the at least two of the plurality of actuation assemblies from the corresponding motors can include actuating a switch to move a coupling on a shaft having the drive gear mounted thereon away from and out of engagement with the motor.

In another embodiment, actuating the bailout assembly includes rotating a tool coupled to the bailout assembly to counter rotate the at least two of the plurality of actuation assemblies. Actuating the bailout assembly can cause a bailout gear to rotate, which in turn causes a gear on each of the at least two of the plurality of actuation assemblies to rotate. In other aspects, the tool can include a plurality of indicators and each indicator can indicate when an actuation assembly coupled thereto has failed.

BRIEF DESCRIPTION OF THE DRAWINGS

The invention will be more fully understood from the following detailed description taken in conjunction with the accompanying drawings, in which:

FIG. 13 illustrates a perspective view of a bailout mechanism of another embodiment of a puck of a tool assembly;

FIG. 14 illustrates a perspective view of the bailout mechanism of FIG. 13;

FIG. 15 illustrates another perspective view of the bailout mechanism of FIG. 14;

FIG. 16 illustrates a perspective view of another embodiment of a puck of a tool assembly with bailout mechanisms;

FIG. 17 illustrates a perspective view of the puck of FIG. 16;

FIG. 18 illustrates a side view of the puck of FIG. 16;

DETAILED DESCRIPTION OF THE INVENTION

Figure 1:
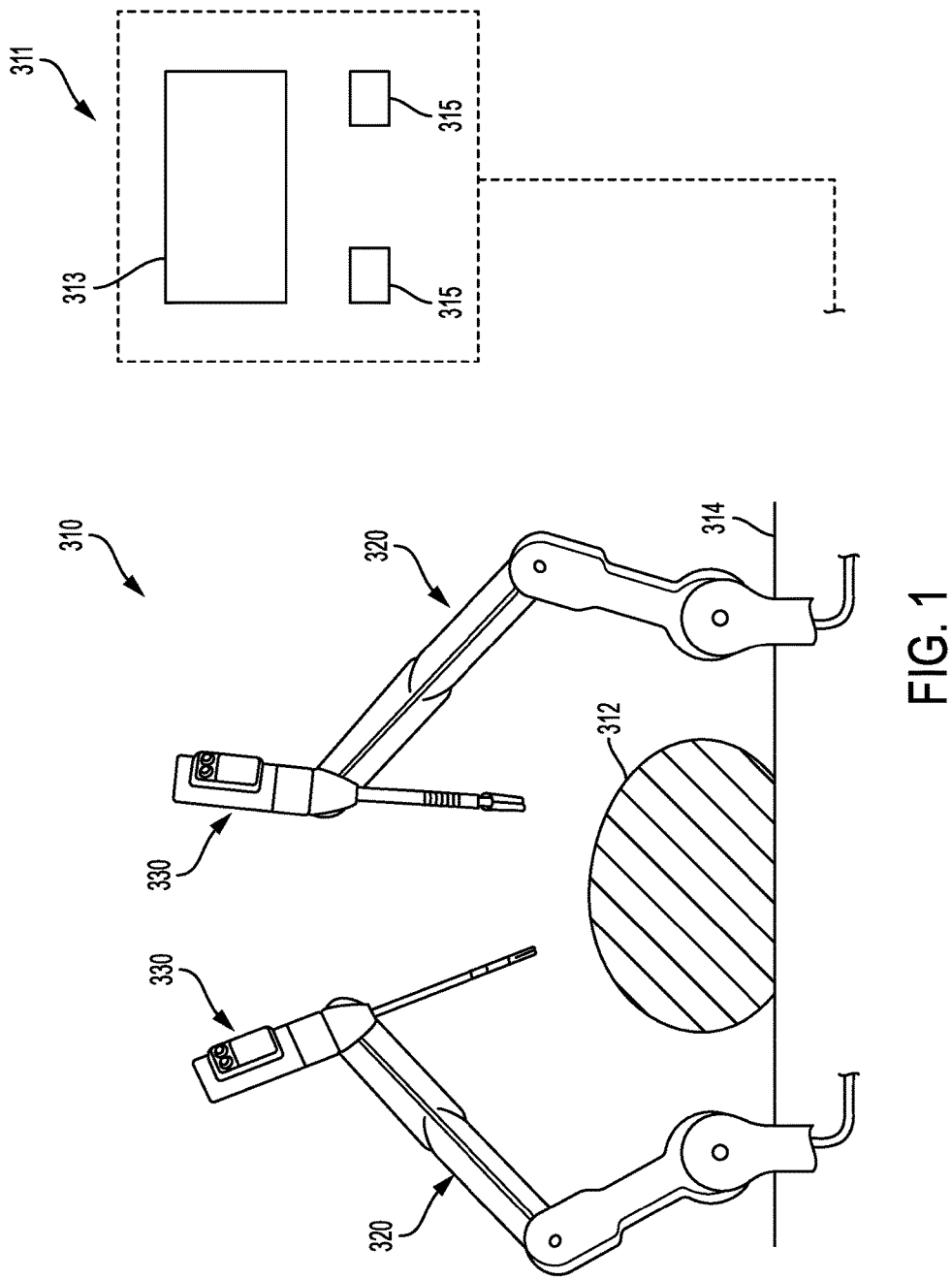
FIG. 1 illustrates a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical tools with bailout mechanisms are provided. Robotic surgical tools generally have a housing and an elongate tool shaft extending from the housing and having an end effector on a distal end thereof. The housing has a plurality of actuators for causing various functions of the end effector, such as rotation, articulation, clamping, firing, stapling, etc. The housing attaches to a tool driver on a robotic arm that electromechanically drives the actuators to control the end effector.

Robotic surgical tools provided herein have various bailout mechanisms in the housing for retracting an actuator or a plurality of actuators in the event of a failure. Bailout mechanisms provided herein can be used to selectively bailout individual actuators, and other bailout mechanisms provided herein can be used to simultaneously bailout one or more actuators at the same time. Various bailout mechanisms thus allow direct engagement with one or more actuators to provide rapid and effective bailout (such as release, reversal, and/or retraction) of surgical tools while minimizing the amount of force and/or time to complete the bailout.

If the system experiences a gear tooth failure in the gear train, an approach can be to drive the gears connected to the gear with a gear tooth failure and/or drive the gear with a gear tooth failure through alternative means.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
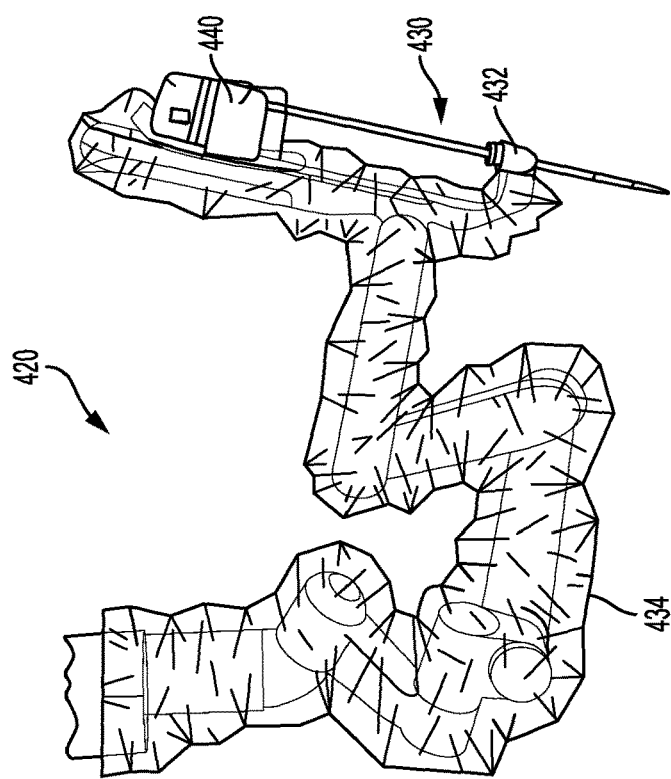
FIG. 2 illustrates an embodiment of a robotic arm of a surgical robotic system with a tool assembly releasably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

Figure 4:
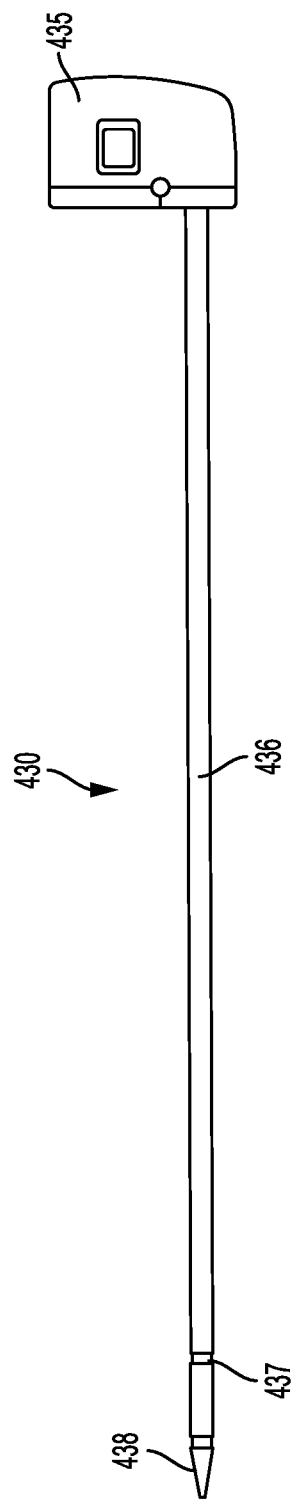
FIG. 4 illustrates the tool assembly of FIG. 2 uncoupled from the robotic arm, the tool assembly including a shaft extending from a puck at a proximal end and having an end effector located at a distal end of the shaft.

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 4. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
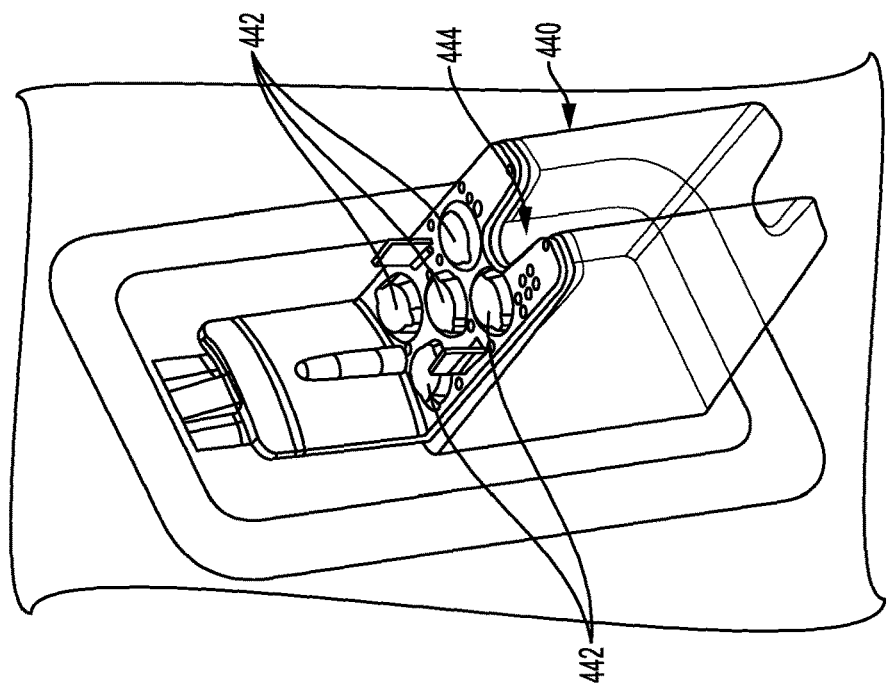
FIG. 3 illustrates a tool driver of the robotic arm of FIG. 2.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

FIG. 4 illustrates the tool assembly 430 uncoupled from the robotic arm 420. The tool assembly 430 includes a housing or puck 435 coupled to a proximal end of a shaft 436 and an end effector 438 coupled to a distal end of the shaft 436. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
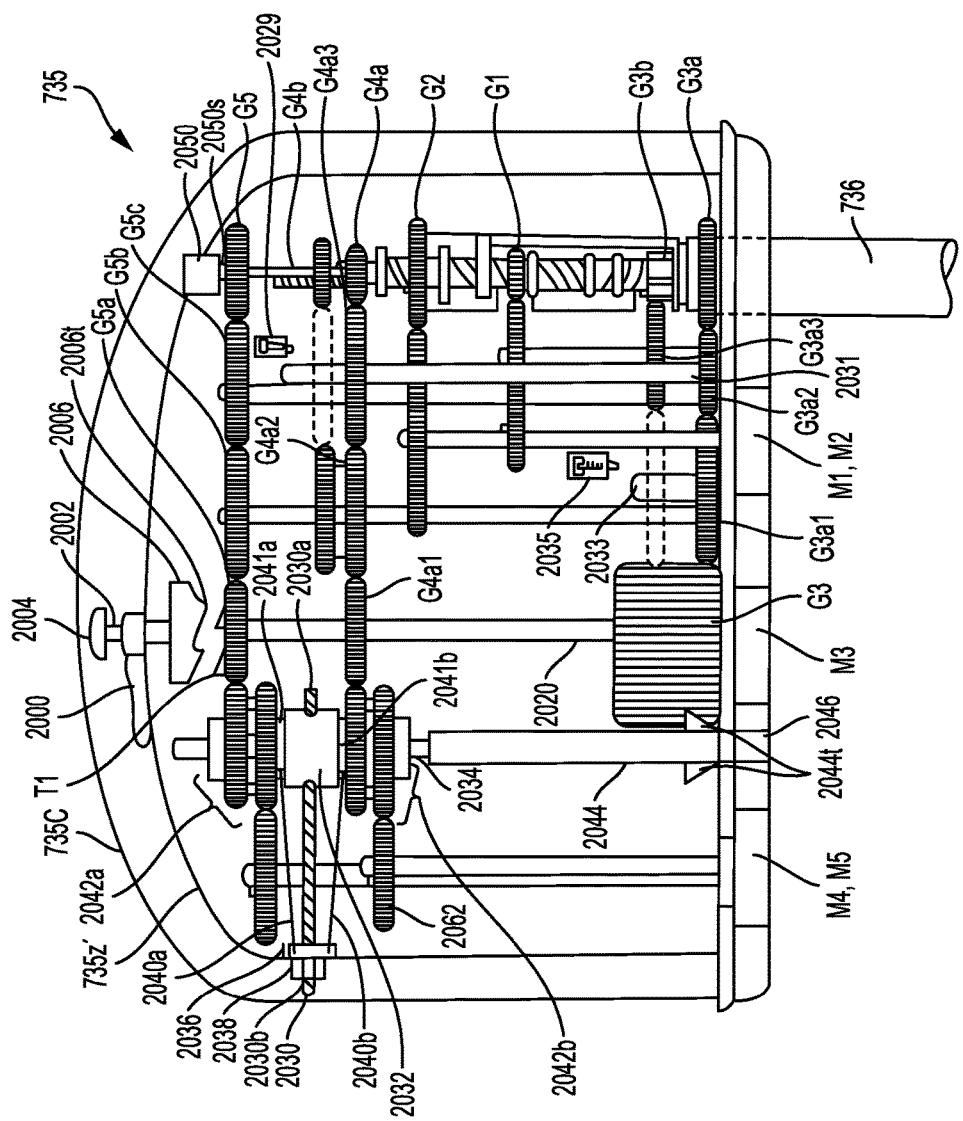
FIG. 5 illustrates the puck of the tool assembly of FIG. 4.

FIG. 5 illustrates an embodiment of a puck 735 and a proximal end of a shaft 736 extending from the puck 735. As shown in FIG. 5, the puck 735 includes a plurality of actuation gears and gear shafts that can be either directly or indirectly controlled by any one of the motors 442 associated with the driver 440. For example, as shown in FIG. 5, the puck 735 is configured to couple to five motors at the locations indicated by reference numbers M1, M2, M3, M4, and M5. In this embodiment, puck 735 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 438 in desired left and right directions. The puck 735 also includes a shaft rotation gear G3a that is coupled to the third motor M3 via a series of one or more additional gears and shafts. Actuation of the third motor M3 will thus rotate the shaft rotation gear G3a thereby causing rotation of the shaft 436 of the tool assembly 430. The third motor M3 can also be configured to shift and to couple, via a series of one or more additional gears and shafts, to a head rotation gear G3b, which will cause rotation of the end effector 438 relative to the shaft 436. The puck 735 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector 438. The puck 735 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector 438. Finally, the illustrated puck 735 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 438.

Figure 6:
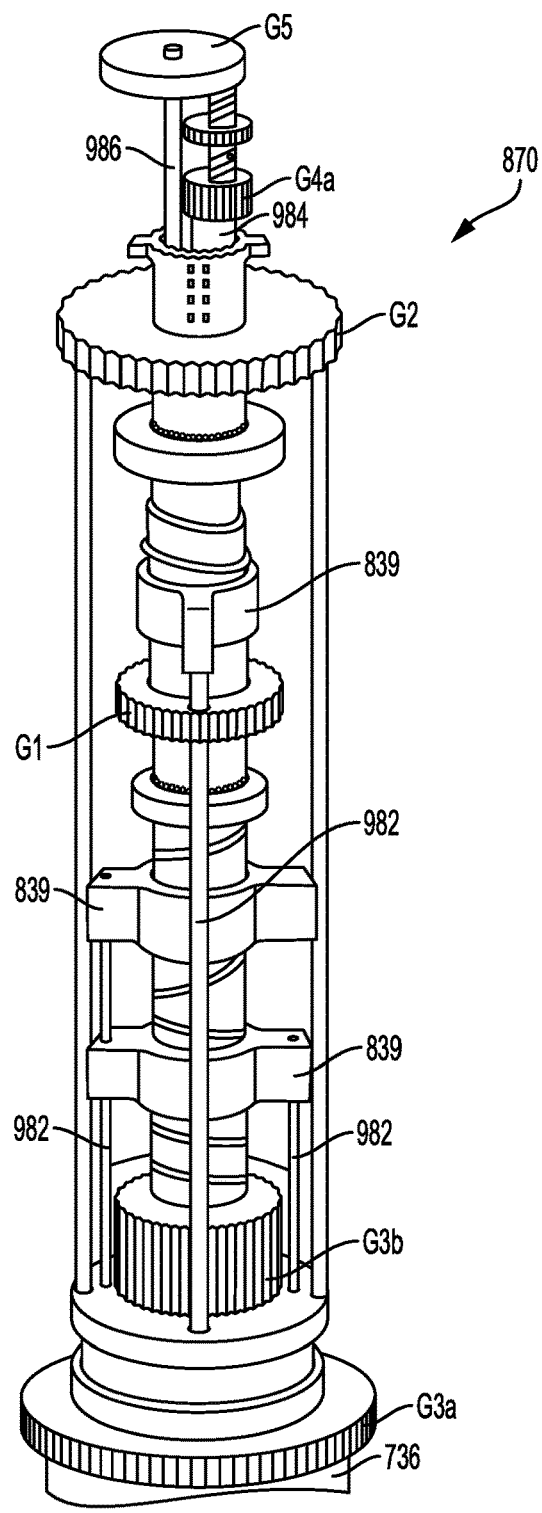
FIG. 6 illustrates an actuation assembly of the puck of FIG. 5.

FIG. 6 illustrates the actuation assembly 870 components of the puck of FIG. 5. As shown and indicated above, each of the gears G1-G5 is coupled to an actuation shaft that extends from the actuation assembly 870 and along the shaft 436 of the tool assembly 430, such as for controlling the movements of the end effector. FIG. 6 illustrates articulation cables 982 that, when actuated (e.g., pushed, pulled, rotated), will cause articulation of the end effector 438 (e.g., movement up, down, left, right, and combinations thereof) relative to the proximal end of the shaft 436. The articulation cables 982 are connected to the articulation couplers 839, shown in FIG. 6, that are driven proximally and distally when the articulation gears G1, G2 are actuated by the first and second motors M1, M2. The actuation assembly 870 also includes an upper rotary driver 984 that when actuated can cause the pair of jaws of the end effector 438 to firmly close. The upper rotary driver 984 is coupled to the firm close gear G4a shown in FIG. 6 such that rotation of the firm close gear G4a by the motor M4 causes rotation of the rotary driver 984. The actuation assembly 870 can also include a lower rotary driver 986 that when actuated can cause movement of a sled located at the end effector 438. The lower rotary driver 986 is coupled to the firing gear G5 shown in FIG. 6 and it likewise rotates in response to rotation of the firing gear G5. A linear pull cable is coupled to the quick close gear G4b shown in FIG. 6 and moves linearly in a proximal direction to cause rapid close of the pair of jaws.

Figure 7:
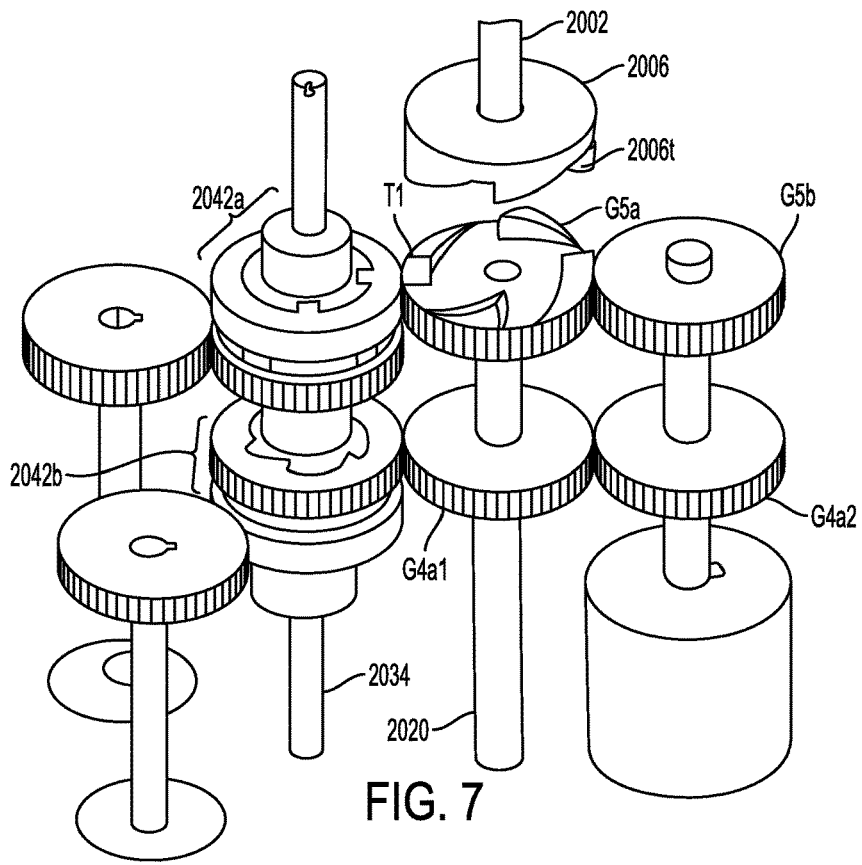
FIG. 7 illustrates engaged gears of the puck of FIG. 5.

Two embodiments of bailout mechanisms are disposed in the puck 735 of FIG. 5 and are configured to engage, drive, reverse, and/or otherwise affect the actuation assembly 870 of FIG. 6. As illustrated in FIG. 5, a crank arm 2000 is disposed external to an inner cover 735i of the puck 735 but internal to an outer cover 735c of the puck 735. The crank arm 2000 is disposed on a shaft 2002 extending through an opening or hole in the inner cover 735i, and the crank arm 2000 is configured to rotate about an axis of the shaft 2002. The shaft 2002 is longitudinally slidable relative to the crank arm 2000, and has a button 2004 on a proximal end thereof. The button 2004 is configured to be manually pushed distally and is configured to engage the crank arm 2000 through various means, for example pins, tabs, hooks, etc., such that rotating the crank arm 2000 will rotate the button 2004 and thus the shaft 2002. The shaft 2002 has a one-way gear 2006 on a distal end thereof. The one-way gear 2006 has a circular shape with teeth 2006t extending distally from a distal surface thereon. The teeth 2006t are shaped such that they can engage corresponding teeth and apply a rotation force in one direction only, as illustrated in FIG. 7. The shaft 2002 is displaced longitudinally proximal to a drive shaft 2020, which has spur gears G5a and G4a1 fixed thereon. Spur gear G5a is rotatably coupled in a gear train with gears G5b and G5c, terminating in the firing gear G5. The spur gear G5a also has teeth T1 extending proximally from a proximal surface thereof. The teeth T1 correspond to teeth 2006t and are configured to engage teeth 2006t and receive a rotation force in one direction only. The spur gear G4a1 is rotatably coupled in a gear train with gears G4a2 and G4a3, terminating in the firm close gear G4a. We note that drive shaft 2020 is displaced longitudinally proximal to the motor M3, and is not coupled to motor M3.

A threaded shaft 2030 is disposed laterally from the drive shaft 2020 and is disposed proximal to the motors M4, M5. A first end 2030a of the threaded shaft 2030 passes through a housing 2032 that is disposed on a shaft 2034 such that the threaded shaft 2030 is rotatable about its longitudinal axis relative to the housing 2032. The shaft 2034 has a series of gears fixed thereto. One or more additional gears and shafts are engageably coupled to the series of gears and the shaft 2034, and are also engaged with the motors M4, M5. As motors M4, M5 are driven, the series of gears on the shaft 2034 are part of gear trains that engage and rotate spur gear G5a and spur gear G4a1 and ultimately the firing gear G5 and the firm close gear G4a. A second end 2030b of the threaded shaft 2030 passes through a displacement nut 2036, through a hole in the inner cover 735i, and through a bailout bolt 2038. The bailout bolt 2038 rests against an external surface of the inner cover 735i and is fixedly attached to the threaded shaft 2030 such that rotation of the bailout bolt 2038 rotates the threaded shaft 2030. The displacement nut 2036 is inside the housing and is threadably disposed on and translates along the threaded shaft 2030. Two metal rods 2040a, 2040b are pivotally fixed to the displacement nut 2036 on a proximal and distal side, respectively, by a variety of different means, such as using pivot pins, embedding ends of the rods 2040a, 2040b therein, etc. The two rods 2040a, 2040b extend proximally and distally from the displacement nut 2036 and fixedly terminate on gear assemblies 2042a, 2042b, respectively, that are both part of the gear series on the shaft 2034 and that are longitudinally slidable on the shaft 2034. The gear assembly 2042a couples through gear trains and shafts to the fifth motor M5 and is part of the gear train that rotates the firing gear G5. The gear assembly 2042b couples through the gear trains and shafts to the fourth motor M4 and is part of the gear train that rotates the firm close gear G4a. The two rods 2040a, 2040b are pivotally fixed on the gear assemblies 2042a, 2042b in a variety of ways, such as by pivot pins, embedding ends of the rods 2040a, 2040b therein, etc.

During normal operation as illustrated in FIG. 5, the gear assemblies 2042a, 2042b remain engaged in the gear trains connecting the motors M4, M5 to the firm close gear G4a and the firing gear G5, respectively. The motors M4, M5 can cause rotation of the firm close gear G4a and the firing gear G5 as explained above. The displacement nut 2036 rests at an inner edge of the inner cover 735i directly opposite the bailout bolt 2038 placed on the outside of the inner cover 735i. The threaded shaft 2030 does not rotate. The shaft 2002 remains in a proximal position, keeping the one-way gear 2006 disengaged from any surrounding gears and the button 2004 proximal to the crank arm 2000 and the inner cover 735i. The shaft 2002 is kept in a proximal position through friction interaction with the hole in the inner cover 735i through which the shaft 2002 passes, but the shaft 2002 can be kept proximal through a variety of other means, such as by a spring disposed around the shaft 2002 between the crank arm 2000 and the button 2004 that will bias the shaft 2002 and the button 2004 proximally. The crank arm 2000 is immobile. The outer cover 735c covers all components that are external to the inner cover 735i.

Figure 8:
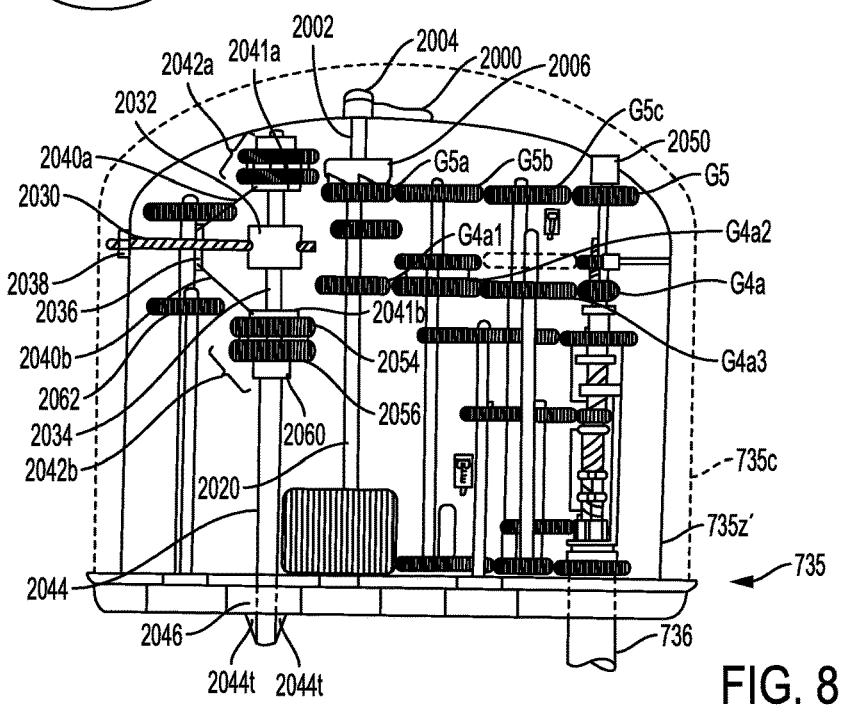
FIG. 8 illustrates the puck of FIG. 5 during bailout.

When bailout is desired, such as when a malfunction occurs in the end effector 438 in the firing and/or firm close functions, the outer cover 735c can be removed. A user can manually rotate the bailout bolt 2038, which will cause rotation of the threaded shaft 2030 because the bailout bolt 2038 is fixed on the threaded shaft 2030. As the threaded shaft 2030 rotates, the displacement nut 2036 will translate along the threaded shaft 2030 toward the housing 2032 because the displacement nut 2036 is threadably disposed on the threaded shaft 2030. Movement of the displacement nut 2036 will cause the metal rods 2040a, 2040b to pivot relative to the displacement nut 2036 and the gear assemblies 2042a, 2042b, thereby forcing the gear assemblies 2042a, 2042b to move proximally and distally on the shaft 2034. In particular, the metal rods 2040a, 2040b will apply proximal and distal forces to the gear assemblies 2042a. 2042b as the metal rods 2040a, 2040b move toward the housing 2032 (and consequently toward the shaft 2034) with the displacement nut 2036. As the gear assemblies 2042a, 2042b move proximally and distally, the gear assemblies 2042a, 2042b will move out of engagement with the gear trains that engage the motors M4, M5 to the firm close gear G4a and the firing gear G5. As illustrated in FIG. 8, the gear assemblies 2042a, 2042b will move entirely out of engagement, thus severing any engagement between the motors M4, M5 and the gears G4a, G5. When the gear assemblies 2042a, 2042b have moved out of engagement of the gear trains, any actuation of the motors M4, M5 will have no effect on the actuation assembly 870. The button 2004 can then be manually pushed distally by a user, which will cause the shaft 2002 to move distally. The button 2004 will couple to the crank arm 2000, and the teeth 2006t on the one-way gear 2006 will engage the teeth T1 on the spur gear G5a. The crank arm 2000 can then be rotated by a user to rotate the spur gear G5a, the shaft 2020, and the spur gear G4al together because they are all fixed to one another. Rotation of the crank arm 2000 causes rotation of the gear trains containing gears G5a, G5b, G5c, and G5 and gears G4a1, G4a2, G4a3, and G4a. The teeth 2006t, T1 only allow engagement and rotation in one direction, thus ensuring that rotation of the crank arm 2000 causes retraction and bailout of the firing and firm close functions.

In some embodiments, a hollow outer shaft 2044 extends around the shaft 2034 and rests distal to the gear assembly 2042b. The outer shaft 2044 is longitudinally slidable around the shaft 2034 and has one or more tabs 2044t on a distal end thereof that flare proximally. A channel 2046 sized to receive the shaft 2044 extends through a distal end of the puck 735. During normal operation, the outer shaft 2044 remains at rest, and the tabs 2044t remain inside the puck 735 and flare out to engage edges of the channel 2046 and prevent the outer shaft 2044 from sliding through the channel 2046. During bailout as the gear assembly 2042b is forced distally as described above, the gear assembly 2042b contacts a proximal end of the outer shaft 2044 and begins to force the outer shaft 2044 distally with continued movement of the gear assembly 2042b. As the outer shaft 2044 is forced distally, the tabs 2044t are forced into the channel 2046 and begin to compress because of their proximal flared shape, allowing the tabs 2044t and the outer shaft 2044 to enter the channel 2046. When the gear assembly 2042b is in its distal-most position, the tabs 2044t will pass entirely through the channel 2046, and the tabs 2044t and a distal end of the outer shaft 2044 will be positioned outside the puck 735, as illustrated in FIG. 8. Because of the proximal flared shape of the tabs 2044t, the tabs 2044t will engage an outer surface of the puck 735 and prevent the outer shaft 2044 from being moved entirely back into the puck 735. Protuberance of the outer shaft 2044 prevents the puck 735 from being correctly reengaged with the tool driver 440, which will prevent the puck 735 from being used again in a future operation after a bailout was required. Faulty pucks may be prevented from being used again through this mechanism.

Another bailout mechanism is illustrated in FIGS. 5 and 8 in the form of a tool receiver 2050. The tool receiver 2050 is configured to receive a tool, such as a hex wrench, and it is displaced longitudinally proximal to the actuation assembly 870. The tool receiver 2050 is fixedly attached to a shaft 2050s that is rotatably engaged with the upper and lower rotary drivers 984, 986 through gear engagements inside of the actuation assembly 870. The tool receiver 2050 extends through the inner cover 735i. During normal operation, the tool receiver 2050 rotates with the actuation assembly 870 and is covered by the outer cover 735c. When bailout is desired, such as when a malfunction occurs in the end effector 438 in the firing and/or firm close functions, the outer cover 735c can be removed, and a user can manually insert a tool such as a hex wrench into the tool receiver 2050 configured to receive such a tool. The user can then rotate the tool, which causes direct application of rotational force to the shaft 2050s and the upper and lower rotary drivers 984, 986. The user can reverse and/or retract the firing and firm close functions by continued rotation of the tool. Various bailout embodiments can be actuated while the puck is still attached to a robotic arm and/or the bailout can be actuated only after being removed from the robotic arm. In other embodiments, linear drive members can also be uncoupled from any motor and/or gear train and pulled axially to bailout any functions associated with the drive members.

While FIGS. 5 and 8 illustrate various embodiments of bailouts, other embodiments are possible. Failures in surgical tools can take a variety of forms and modes, and can require a variety of different responses depending on the specifics of each situation. For example, if there is a failure in the motor in which the motor is locked in place, a possible bailout approach is to disengage a drive gear from a gear train and provide alternative power to the drive train. The rest of the drive train can be parked during the transition. If a motor is free-spinning, an approach can be to stop any free spinning condition before any harm occurs to the patient and/or the surgical tool by using approaches such as dampeners or intentional friction or clamps/locks in the system that can be overcome but prevents unintentional motion. An approach can also be to sense or detect a difference between actual and requested motion to engage a bailout safely, and engage a drive train with another source of motor activity to allow a safe bailout and/or replacement. More than one motor can also be engaged with any critical drive system to account for any motor failure. While this approach requires multiple motors per critical drive system, less expensive motors can be used and successful bailout and/or operation can be assured because of backup motors being present. If failure occurs in a gear train, it can happen in a variety of ways. For example, a gear train can be locked in place. In such a failure, a bailout approach can be to disengage a distal-most gear and provide alternative power to the drive train. If a weak link in the gear train is present and a user and/or the system knows where the weak link is, an approach can be to disengage the drive train just distal to the weak link and provide alternative power at that location. A weak link can also be designed into a system such that a user and/or the system will always know which link will fail if a failure occurs. If the gear train is unable to translate power, an approach can be to stop any free spinning condition before any harm occurs to the patient and/or the surgical tool by using approaches such as dampeners or intentional friction or clamps/locks in the system that can be overcome but prevents unintentional motion. The drive train can be engaged with another source of motor activity to allow a safe bailout and/or replacement. If the system experiences a loss of controls and/or power, a mechanical bailout can be used that does not require power and can be operated entirely manually. Another approach can be to provide a battery powered backup within a robotic arm with sufficient power to return the system to a home and/or retracted and/or bailout position to allow for safe removal and/or replacement of any malfunctioning components.

Figure 9:
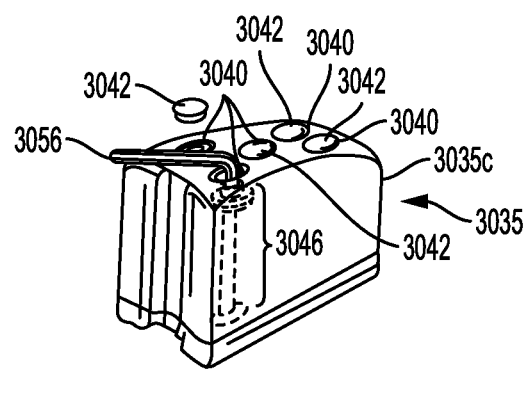
FIG. 9 illustrates a perspective view of one embodiment of a puck of a tool assembly with selective bailout mechanisms.
Figure 10:
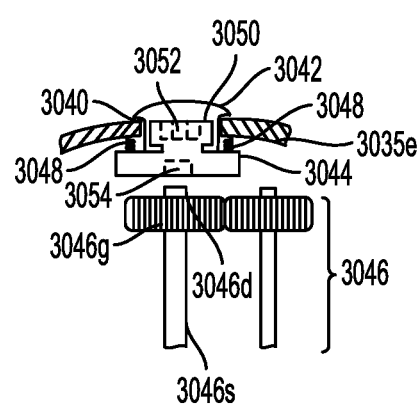
FIG. 10 illustrates a cross-sectional view of one of the bailout mechanisms of FIG. 9.
Figure 11:
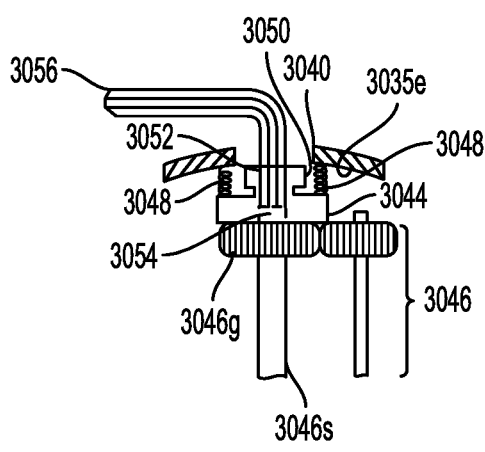
FIG. 11 illustrates a cross-sectional view of the bailout mechanism of FIG. 10 with a bailout tool engaged.

FIGS. 9-11 illustrate additional embodiments of bailout mechanisms that allow for selective bailout of selected functions. FIG. 9 shows a puck 3035 similar to the puck 735 of FIG. 5, but which has selective bailouts for actuators that are actuated by each motor. The puck 3035 is configured to couple to five motors M1. M2, M3, M4, and M5 and includes an actuation assembly with gears similar to the actuation assembly 870 that is configured to allow actuation of a variety of functions in an end effector and/or an elongate shaft as explained above with regards to FIGS. 5-8. The puck 3035 however has five openings 3040 through a cover 3035c, with each opening 3040 corresponding to a series of one or more additional gears and shafts that engage the motors M1, M2, M3, M4, and M5 to the actuation assembly. Each opening can be covered by a rubber cap 3042 that is sized and shaped to sit in and seal each opening 3040, as illustrated in FIG. 10. The rubber caps 3042 each also seal around a bailout gear 3044 disposed in each of the openings 3040. The bailout gears 3044 have a ledge feature 3050 to ensure a secure seal with each rubber cap 3042. Each bailout gear 3044 has a cannulated tool receiver 3052 on a proximal side thereof and a cannulated shaft receiver 3054 on a distal side thereof and opposite to the cannulated tool receiver 3052. The cannulated tool receiver 3052 is configured to receive a tool therein, such as a hex wrench, a screw driver, etc. The cannulated shaft receiver 3054 is configured to receive a proximal end of a drive shaft from one of the series of gears and shafts inside the puck 3035 and engaged between the motors M1, M2, M3, M4, M5 and the actuation assembly. Each opening 3040, rubber cap 3042, and bailout gear 3044 is displaced longitudinally proximal to a gear and shaft assembly 3046 that corresponds with each of the five motors M1, M2, M3, M4, and M5. As illustrated in FIG. 10, each gear and shaft assembly 3046 has a gear 3046g positioned directly distal to the bailout gear 3044 and fixed on a shaft 3046s with a proximal end 3046d of the shaft protruding proximal to the gear 3046g. Each cannulated shaft receiver 3054 and each proximal end 3046d of the shaft 3046s are configured to engage one another such that rotation of the bailout gear 3044 causes rotation of the gear 3046g. For example, the cannulated shaft receiver 3054 can have a hexagonal opening and the proximal end 3046d can have a hexagonal cross section. The bailout gears 3044 are coupled to an inside edge 3035e of the puck 3035 by two springs 3048. The springs 3048 bias each bailout gear 3044 proximally out of engagement with each shaft 3046s and into each opening 3040.

During normal operation, the rubber caps 3042 are disposed in the openings 3040 and seal around the bailout gears 3044. The bailout gears 3044 are held proximally from the gear and shaft assemblies 3046 by the springs 3048, and the gear and shaft assemblies 3046 engage with various gear trains in the puck 3035 to allow the motors M1, M2, M3, M4, M5 to actuate functions in an elongate shaft coupled to the puck 3035 and/or an end effector disposed on a distal end of the elongate shaft.

When bailout is desired, such as when one or more functions of the elongate shaft and/or the end effector fail and need to be reversed, a user can locate the opening 3040 that corresponds to the motor M1, M2, M3, M4, M5 and subsequent gear and shaft assembly 3046 for the function that has failed. The user can remove the corresponding rubber cap 3042 and place a tool 3056, such as a hex wrench, a screw driver, etc., into the cannulated tool receiver 3052. Applying distal force to the tool 3056 to overcome spring bias from the springs 3048 moves the bailout gear 3044 distally and into engagement with the proximal end 3046d of the shaft 3046s of the gear and shaft assembly 3046. The user can rotate the tool 3056, which will cause rotation of the bailout gear 3044 and the gear and shaft assembly 3046 and translate into rotation of the corresponding gear on the actuation assembly. As the corresponding gear on the actuation assembly is rotated, retraction and/or bailout of the selected function occurs. Selected functions can therefore be bailed out, allowing a user to bail out one function without having to bail out all functions at once. A user can, for example, bail out one function before another or only bail out one function in total, thus providing greater flexibility and ease of use to surgeons during an operation.

Figure 12:
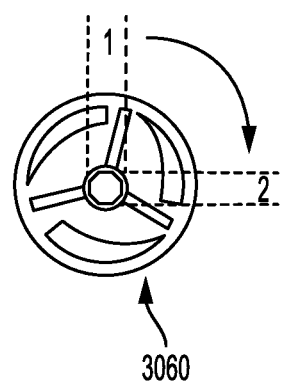
FIG. 12 illustrates an embodiment of a torque limiter that can be used with the puck of FIG. 9.

There can be a variety of other embodiments. For example, the bailout gear can include a one-way gear similar to the one-way gear 2006 of FIG. 5. In such an embodiment, the bailout gear would not have a shaft receiver and the gear and shaft assembly would not have a proximal end protruding above the gears. The bailout gear can also incorporate a torque limiter 3060, as illustrated in FIG. 12. The torque limiter 3060 can be incorporated into the bailout gear and can be configured to limit a torque applied to the bailout gear and/or the interaction between the bailout gear and the gear and shaft assembly by slipping (as in a friction plate slip-clutch) or by uncoupling the load entirely (as in a shear pin) such that the torque limiter 3060 may protect the gears and shafts within the puck from damage by mechanical overload applied to the tool 3056 by the user.

In the embodiments described in FIGS. 9-11, gears in gear trains with the actuation assembly remain engaged within their respective gear trains even during bailout. In other embodiments, it is possible for gears to disengage from their respective gear trains when bailout is desired. For example, FIGS. 13-15 illustrate an embodiment of a gear and shaft assembly 3070 similar to the gear and shaft assembly 3046 described above in FIGS. 9-11. As in FIGS. 9-11, the gear and shaft assembly 3070 is disposed within a puck and gears 3072, 3074 engage in a gear train between one of the motor M1, M2, M3, M4, M5 and an actuation assembly. A user can access the gear and shaft assembly 3070 through one or more openings in a cover of the puck, and the user can rotate the gear and shaft assembly 3070 with a tool to bailout a function that has failed. However the gear and shaft assembly 3070 provides a mechanism to disengage the gear 3074 from the gear train when bailout is desired. The gear 3074 is disposed on a shaft 3076 similar to the shaft 3046s of FIGS. 9-11. The shaft 3076 has a tool receiver 3078 disposed on a proximal end thereof that is configured to receive a tool for rotating the shaft 3076, for example having a slot sized and configured to receive a screw driver. The shaft 3076 also has a collar 3080 disposed around the proximal end of the shaft 3076 and that is longitudinally slidable. The shaft 3076 also has a spring arm 3082 that is coupled adjacent to a proximal end of the shaft and that is configured to flatten and rest in a groove 3076g on the shaft 3076. The spring arm 3082 has a flat portion 3082f in a middle of the spring arm 3082 sized and shaped to receive the gear 3074 therearound and configured to slide distally along the groove 3076g upon application of distal force on the spring arm 3082. The spring arm 3082 has an extending portion 3082e on a distal end thereof configured to engage a distal edge of the gear 3074 to keep the gear 3074 from sliding distally along the shaft 3076 because the extending portion 3082e is biased proximally.

During normal operation, the gears 3072, 3074 remain engaged with one another and remain engaged in a gear train between one or more of the motors M1, M2, M3, M4, M5 and the actuation assembly. The spring arm 3082 acts proximally on the gear 3074 to keep the gear 3074 engaged in the gear train such that actuation of one or more of the motors M1, M2, M3, M4, M5 will translate rotational actuation through the gear train and to the actuation assembly, thus actuating one or more functions on an elongate shaft and/or an end effector on the elongate shaft. The collar 3080 remains proximally displaced from the spring arm 3082 and remains around the tool receiver 3078 through frictional interaction.

When bailout is desired, such as when one or more functions of the elongate shaft and/or the end effector fail and need to be reversed, a user can locate a corresponding opening and the corresponding gear and shaft assembly 3070. The user can place a tool 3084, such as a screw driver, a hex wrench, etc., onto the tool receiver 3078. Because the collar 3080 extends around the tool receiver 3078, placing the tool 3084 onto the tool receiver 3078 includes contacting and forcing the collar 3080 to move distally along the shaft 3076. As the collar 3080 is forced distally through contact with the tool 3084, the collar 3080 slides over a proximal portion of the spring arm 3082, overcoming a spring bias of the spring arm 3082 and forcing the spring arm 3082 to flatten into the groove 3076g on the shaft 3076, as illustrated in FIG. 14. As the spring arm 3082 is flattened into the groove 3076g, the extending portion 3082e of the spring arm 3082 flattens with the rest of the spring arm 3082 and disengages from the gear 3074. The extending portion 3082e thus stops providing a proximal force on the gear 3074, and the gear 3074 slides distally through gravitational forces out of engagement with the gear 3072 and any gear train(s) engaged with one or more of the motors M1, M2, M3, M4, M5. The gear 3074 remains engaged through the series of gears and shafts to the actuation assembly by, for example, being engaged with an elongate gear that allows continued engagement between the gear 3074 and the elongate gear even upon distal movement of the gear 3074. As illustrated in FIG. 15, the collar 3080 and the gear 3074 can continue to slide distally such that the gear 3074 is entirely out engagement with any gears engaged with the motors M1, M2, M3, M4, M5, and the spring arm 3082 can return to its position protruding out of the groove 3076g. The tool 3084 can be received into the tool receiver 3078, and the user can rotate the tool 3084 to provide rotational force to the shaft 3076 and bailout a function associated with rotation of the shaft 3076 and the series of gears and shafts between the gear 3074 and the actuation assembly. Rotational force can be easier on the shaft 3076 because the gear 3074 is no longer engaged through any gear trains to one or more of the motors M1, M2, M3, M4, M5, and any actuation of the motors M1, M2, M3, M4, M5 does not translate into rotation of the gear 3074 or the shaft 3076. Select functions can thus be bailed out and/or reversed while not affecting other functions and/or functions can be bailed out in a specific order selectable by the user. In various embodiments, the collar can be manually forced distally to disengage the gear 3074 from the spring arm 3082 if additional force is needed. While in this embodiment various gears are entirely disconnected from one another, in various embodiments, rather than disconnecting a gear and/or gear train entirely from a motor and/or a drive disk or gear driven by a motor, a drive shaft can experience limited or free rotation while still being attached to the motor and/or the drive disk, for example by being slip attached by removing keying between the gear and/or gear train and the drive shaft.

Various embodiments can incorporate indicators that allow a user to identify which gear and shaft assemblies and/or gear trains might be required to bail out a failing function on an elongate shaft and/or end effector and that can indicate an order of bailout (such as indicating an order for which gear and shaft assemblies should be bailed out to retract a firing function before a jaw closure function). As illustrated in FIGS. 16-18, indicators can take the form of lights 3090, 3092, for example LED lights, disposed on an external distal 3094d and/or proximal 3094p surface of a puck 3094 similar to the pucks described above. Each light 3090, 3092 can be configured to blink, flash, change color, or otherwise indicate which gear and shaft assembly should be accessed by a user to bail out a failing function. Each light 3092, 3094 can be electronically coupled to a control system, such as the control system 315 discussed herein. During operation of the device, the lights 3092, 3094 can be configured to indicate a status of various functions, for example indicating that all functions are operating normally (such as showing a green light) or simply remaining in an off state. If there is a mechanical failure such as with one or more functions in an elongate shaft 3096 and/or an end effector disposed on a distal end of the elongate shaft 3096 and/or there is some other error requiring bailout, a corresponding light 3090, 3092 can be configured to indicate a location of the failure and/or error, for example by blinking or turning a different color (such as from green to red). Error locations can be identified in a variety of ways, as further explored in U.S. patent application Ser. No. 15/131,963, filed on Apr. 18, 2016 and entitled "Method for Operating a Surgical Instrument," incorporated herein by reference. In various embodiments with openings in a cover of a puck to allow selected individual bailout, such as the embodiment described above for FIGS. 9-11, lights can be disposed around the openings and can flash or otherwise indicate which opening should be accessed by a user to reverse and/or bail out a failing function. In the embodiment shown in FIGS. 16-18, a portion of a cover of the puck 3094 can be removed by manually pressing a coupling switch 3098 to disengage the portion of the cover and remove it from the puck 3094, thus allowing a user to directly access any gear and shaft assemblies required to bailout a failing function.

Figure 19:
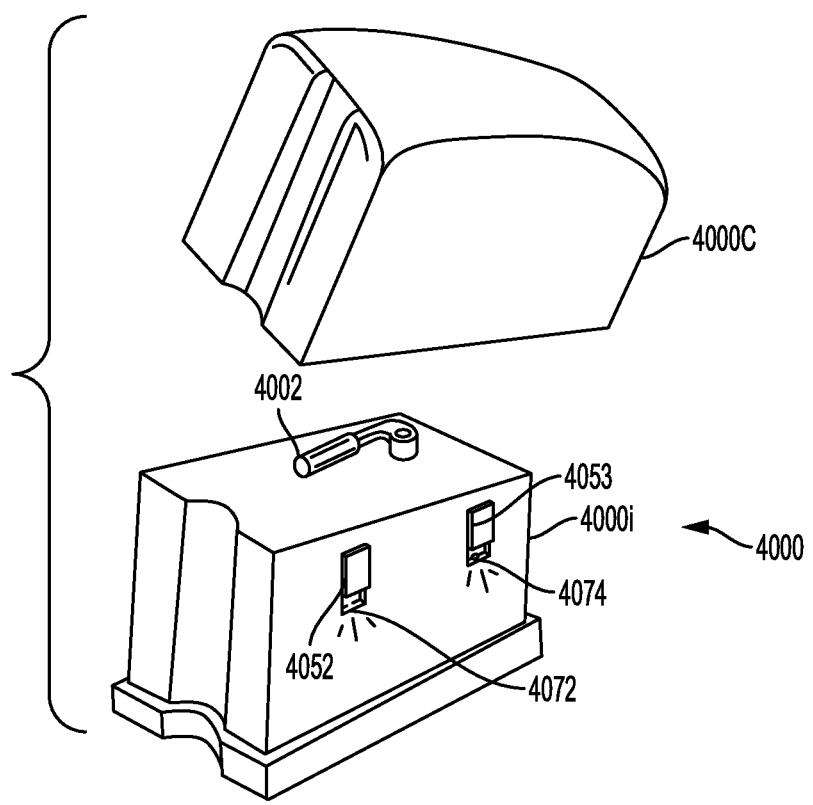
FIG. 19 illustrates a perspective view of one embodiment of a puck of a tool assembly with bailout mechanisms.
Figure 20:
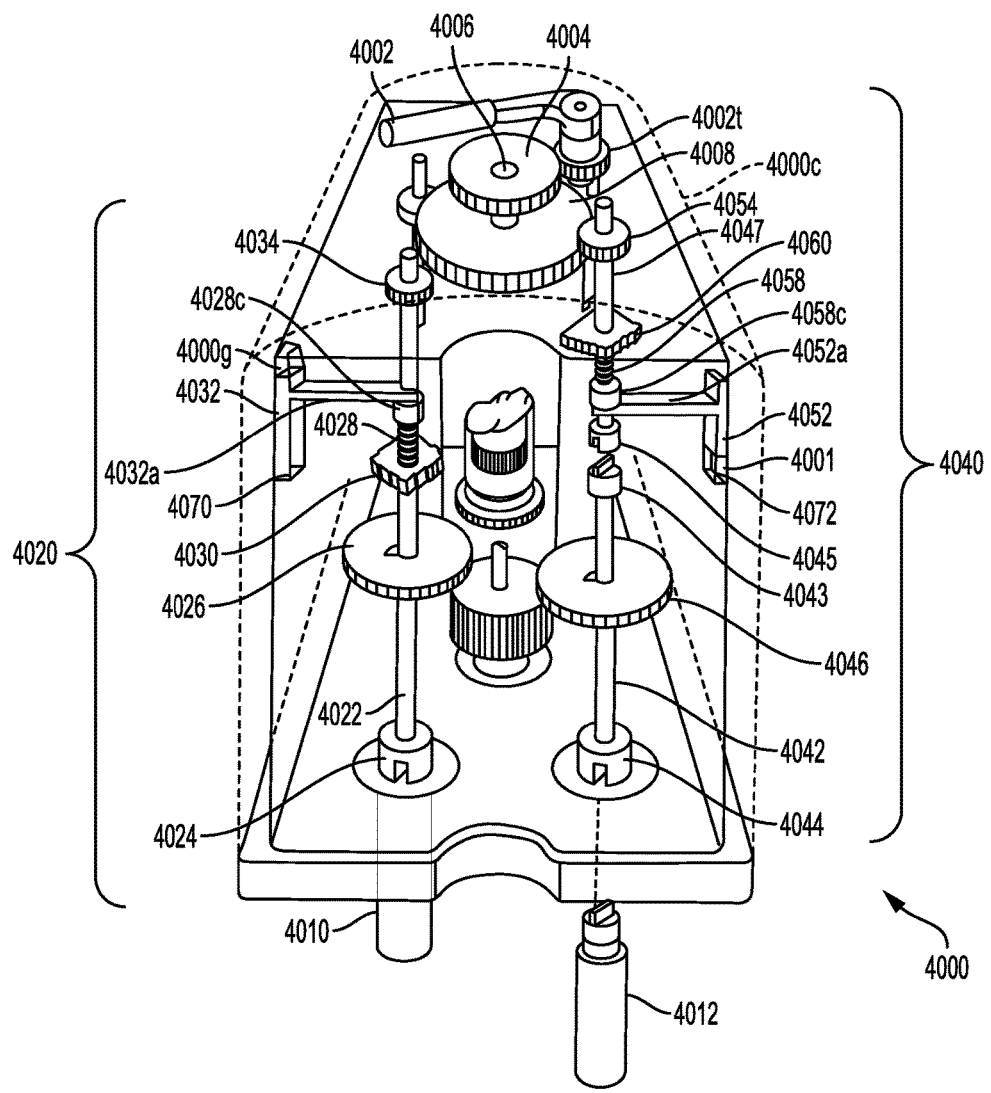
FIG. 20 illustrates a transparent perspective view of the puck of FIG. 19 with the bailout mechanisms.

While selected individual functions can be bailed out, it is also possible to bailout selected functions simultaneously. As illustrated in FIGS. 19-20, a puck 4000 has an outer cover 4000c and an inner cover 4000i. The puck 4000 is similar to the puck 735 disclosed in FIGS. 5-8, but the puck 4000 allows for simultaneous bailouts of selected functions. As illustrated in FIG. 19, the puck has a crank arm 4002 that extends through the inner cover 4000i. Within the inner cover 4000i, the crank arm 4002 engages a first bailout gear 4004 through teeth 4002t on a distal end of the crank arm 4002. The first bailout gear 4004 is fixedly disposed on a proximal end of a drive shaft 4006, to which a second bailout gear 4008 is fixedly attached on a distal end thereof. The first bailout gear 4004, the drive shaft 4006, and the second bailout gear 4008 are configured to rotate together. The puck 4000 has multiple gear and shaft assemblies engageably coupled to motors M1, M2, M3, M4, M5 and that are configured to translate actuation of one or more motors to an actuation assembly similar to that illustrated in FIG. 5. In this embodiment the gear and shaft assemblies have bailout mechanisms disposed thereon. FIG. 20 illustrates two exemplary gear and shaft assemblies 4020, 4040 with bailout mechanisms therein. Gear and shaft assembly 4020 has a shaft 4022 disposed longitudinally proximal to a motor 4010, such as one of the motors M1, M2, M3, M4, M5, and shaft 4022 has a motor coupler 4024 disposed on a distal end thereof that can be, for example, a slot configured to receive a tab on the motor engagement 410 that is configured to rotate the shaft 4022 (and consequently a series of gears and shafts coupled to an actuation assembly not shown in FIG. 20 for the sake of clarity). Shaft 4022 has a gear 4026 fixed thereon that rotates with the shaft 4022 and helps rotate the series of gears and shafts coupled to the actuation assembly. The shaft 4022 has a spring 4028 disposed therearound proximal to the gear 4026 and just proximal but in contact with a brace 4030 that is fixedly disposed in the puck 4000. The shaft 4022 slidably passes through a hole in the brace 4030. A proximal end of the spring 4028 is in contact with a surface of the brace 4030, and a distal end of the spring 4028 terminates in a collar 4028c that is in contact with an arm 4032a of a bailout switch 4032. The collar 4028c is fixedly attached to the shaft 4022 such that longitudinal translation of the collar 4028c causes longitudinal translation of the shaft 4022. The bailout switch 4032 is disposed within the inner cover 4000i of the puck 4000 and is located in a longitudinal groove 4000g in the inner cover 4000i. A portion of the bailout switch 4032 extends out of the inner cover 4000i and is manually slidable longitudinally proximal and distal relative to the cover 4000i. The arm 4032a terminates in a u-shaped notch that is configured to rest around the shaft 4022 and against a proximal side of the collar 4028c of the spring 4028, thus applying a distal force to the spring 4028. The spring 4028 biases the shaft 4022 proximally. A spur gear 4034 is fixedly attached to a proximal end of the shaft 4022 such that rotation of the spur gear 4034 causes rotation of the shaft 4022.

During normal operations, the bailout switch 4032 is disposed distally in the groove 4000g and maintained in position by friction interaction. A distal position of the bailout switch 4032 causes the arm 4032a to rest in a distal position, applying distal force to the collar 4028c and compressing the spring 4028. The shaft 4022 is held in a distal position, causing engagement between the motor coupler 4024 of the shaft 4022 and the motor 4010.

When bailout is desired, such as when one or more functions of an elongate shaft and/or an end effector fail and need to be reversed, a user can remove the outer cover 4000c and manually move the bailout switch 4032 proximally in the groove 4000g. Proximal movement causes the arm 4032a to move proximally, allowing the spring 4028 to decompress and force the collar 4028c proximally. Movement of the collar 4028c causes proximal movement of the shaft 4022, which disengages the motor coupler 4024 of the shaft 4022 from the motor 4010. Proximal movement of the shaft 4022 does not disengage the gear 4026 from the series of gears and shafts, thus rotation of the gear 4026 is translated to the actuation assembly by, for example, having the gear 4026 engage with an elongate gear that remains in engagement with the gear 4026 even with proximal movement. The spur gear 4034 translates proximally with the shaft 4022 such that the spur gear 4034 is brought into engagement with the second bailout gear 4008. Upon pivot of the crank arm 4002, the first bailout gear 4004 rotates, causing rotation of the drive shaft 4006, the second bailout gear 4008, and the spur gear 4034. The shaft 4022 rotates with the spur gear 4034, which rotates the gear 4026 and causes rotation of the actuation assembly through the series of gears and shafts and the bailout of at least one function on the elongate shaft and/or the end effector.

Bailouts in the puck 4000 are not limited to proximal movement, and can incorporate a variety of different bailout mechanisms. For example, the gear and shaft assembly 4040 can have a lower shaft 4042 disposed longitudinally proximal to a motor 4012, such as one of the motors M1, M2, M3, M4, M5, and the lower shaft 4042 can have a motor coupler 4044 disposed on a distal end thereof that can be, for example, a slot configured to receive a tab on the motor engagement 412 that is configured to rotate the lower shaft 4042 (and consequently a series of gears and shafts coupled to an actuation assembly not shown in FIG. 20 for the sake of clarity). The lower shaft 4042 has a gear 4046 fixed thereon that rotates with the lower shaft 4042 and helps rotate the series of gears and shafts coupled to the actuation assembly. The lower shaft 4042 has a distal coupler 4043 on a distal end thereof that engages with a proximal coupler 4045 on a proximal end of an upper shaft 4047, both couplers 4043, 4045 taking the forms of a tab and a slot herein. An arm 4052a of a bailout switch 4052 extends to engage the upper shaft 4047. The arm 4052a terminates in a u-shaped notch that is configured to rest longitudinally slidably against the upper shaft 4047. The bailout switch 4052 is disposed within the inner cover 4000i of the puck 4000 and is located in a longitudinal groove 4001 in the inner cover 4000i. A portion of the bailout switch 4052 extends out of the inner cover 4000i and is manually slidable longitudinally proximal and distal relative to the cover 4000i. The upper shaft 4047 has a spring 4058 disposed therearound proximal to the arm 4052a of the bailout switch 4052. A proximal end of the spring 4058 terminates in a collar 4058c that is in contact with the arm 4052a of the bailout switch 4052. The collar 4058c is fixedly attached to the upper shaft 4047 such that longitudinal translation of the collar 4058c causes longitudinal translation of the upper shaft 4047. The spring 4058 is disposed just distal to but in contact with a brace 4060 that is fixedly disposed in the puck 4000. The upper shaft 4047 slidably passes through the brace 4060 through a hole therethrough. A distal end of the spring 4058 is in contact with a surface of the brace 4060 so that the spring 4058 is compressed between the arm 4052a and the brace 4060. The arm 4052a is configured to apply a proximal force against a distal end of the collar 4058c. The spring 4058 biases the upper shaft 4047 distally. A spur gear 4054 is fixedly attached to a proximal end of the upper shaft 4047 such that rotation of the spur gear 4054 causes rotation of the upper shaft 4047.

During normal operations, the bailout switch 4052 is disposed proximally in the groove 4001 and maintained in position by friction interaction. A proximal position of the bailout switch 4052 causes the arm 4052a to rest in a proximal position, applying a proximal force to the collar 4058c and compressing the spring 4058. The upper shaft 4047 is held in a proximal position, preventing engagement between the upper shaft 4047 and the lower shaft 4042 and between the spur gear 4054 and the second bailout gear 4008. The lower shaft 4042 engages the motor 4012 through the motor coupler 4044.

When bailout is desired, such as when one or more functions of an elongate shaft and/or an end effector fail and need to be reversed, a user can remove the outer cover 4000c and manually move the bailout switch 4052 distally in the groove 4001. Distal movement causes the arm 4052a to move distally, allowing the spring 4058 to decompress and force the collar 4058c distally. Movement of the collar 4058c causes distal movement of the upper shaft, which engages with the lower shaft 4042 through the couplers 4043, 4045. Distal movement of the uppers shaft 4047 does not disengage the gear 4046 from the series of gears and shafts, thus rotation of the gear 4046 is translated to the actuation assembly because the gear 4046 is disposed on the lower shaft 4042. The spur gear 4054 translates distally with the upper shaft 4047 such that the spur gear 4054 is brought into engagement with the second bailout gear 4008. Upon pivot of the crank arm 4002, the first bailout gear 4004 rotates, causing rotation of the drive shaft 4006, the second bailout gear 4008, and the spur gear 4054. The upper shaft 4047 rotates with the spur gear 4054 and causes rotation of the lower shaft 4042 through the couplers 4043, 4045, and the lower shaft 4042 rotates the gear 4046 and causes rotation of the actuation assembly through the series of gears and shafts and the bailout of at least one function on the elongate shaft and/or the end effector. The bailout switches 4032, 4052 can be switched independently of each other or simultaneously. As illustrated in FIG. 19, a plurality of bailout switches 4052, 4053 can be disposed on the inner case 4000*i* of the puck 4000 and correspond to a plurality of functions in the elongate shaft and/or the end effector. When bailout is desired, a user can actuate one or more bailout switches, for example bailout switches 4032, 4052, 4053, and then pivot the crank arm 4002 to effectively bailout a plurality of function simultaneously.

While the crank arm 4002 as illustrated is a moment arm lever with a pawl, the crank arm can take a variety of forms. For example, in other embodiments a screw head, such as a hex screw head with a ratcheting mechanism, can be used, allowing the insertion of an exterior retraction bar instead of having a fixed arm on the puck. The retraction bar can be ratcheted rather than repeatedly rotating any arm. In other embodiments, each drive shaft coupled to a motor can have a screw head. While bailout switches in the form of switches in grooves are illustrated in FIGS. 19 and 20, a variety of different actuators can be used. For example, the bailout switches can take the form of pull tabs, hooks, buttons, dials, etc. Various embodiments can incorporate indicators that allow a user to identify which gear and shaft assemblies and/or gear trains might be required to bail out a failing function on the elongate shaft and/or end effector. As illustrated in FIGS. 19-20, indicators can take the form of lights 4070, 4072, 4074, for example LED lights, disposed on an external surface of the puck 4000, and each light 4070, 4072, 4074 can be configured to blink, flash, change color, or otherwise indicate which gear and shaft assembly should be accessed by a user to bail out a failing function. While three lights are illustrated, a plurality of lights can be used, one for each function and/or one for each motor. Each light 4070, 4072, 4074 can be electronically coupled to a control system, such as the control system 315 discussed above.

During operation of the device, the lights 4070, 4072, 4074 can be configured to indicate a status of various functions, for example indicating that all functions are operating normally (such as showing a green light) or simply remaining in an off state. If there is a mechanical failure such as with one or more functions in the elongate shaft and/or the end effector disposed on a distal end thereof and/or there is some other error requiring bailout, a corresponding light, such as lights 4070, 4072, 4074, can be configured to indicate a location of the failure and/or error, for example by blinking or turning a different color (such as from green to red). Error locations can be identified in a variety of ways, as further explored in U.S. patent application Ser. No. 15/131,963, filed on Apr. 18, 2016 and entitled "Method for Operating a Surgical Instrument," incorporated herein by reference. In various embodiments with bailout switches 4032, 4072, 4074 in the inner cover 4000*i* of the puck 4000, indicators in the form of lights 4070, 4072, 4074 can be disposed on one surface of the grooves of the bailout switches and can flash or otherwise indicate which switch should be actuated to reverse and/or bail out a failing function. In other embodiments, such as when the bailout switches are in the form of pull tabs, indicators can be disposed adjacent to the bailout switches.

There are several general aspects that apply to the various descriptions herein. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 21:
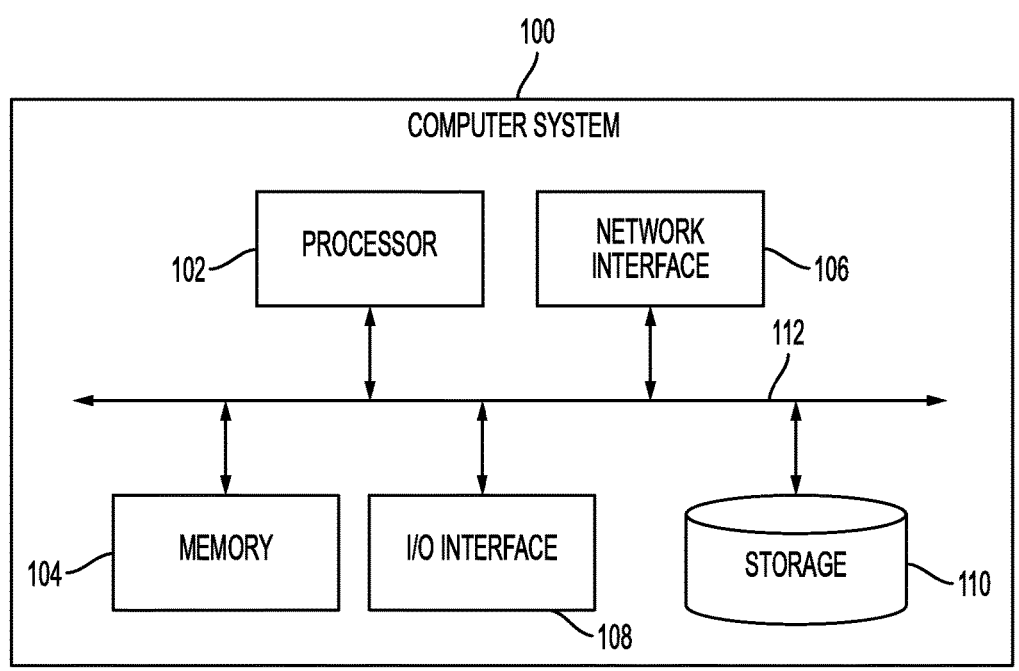
FIG. 21 illustrates one exemplary embodiment of a computer system having one or more features consistent with the present description.

FIG. 21 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 21 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
a housing;
an elongate shaft extending distally from the housing;
an end effector disposed at a distal end of the elongate shaft; and
a plurality of actuation assemblies coupled to a plurality of motor-driven drive gears, each of the motor-driven drive gears being configured to drive a corresponding actuation assembly, each of the actuation assemblies being configured to operate a function of the end effector, and
a bailout mechanism configured to manually drive at least two of the plurality of actuation assemblies simultaneously to reverse the corresponding functions of the end effector.

2. The tool of claim 1, wherein each motor-driven drive gear is selectively movable between a first position, in which the motor-driven drive gear has a coupling positioned to engage an external motor, and a second position, in which the coupling is positioned such that it is prevented from engaging an external motor.

3. The tool of claim 1, wherein the bailout mechanism includes a crank arm configured to engage and drive the at least two actuation assemblies simultaneously.

4. The tool of claim 1, wherein the bailout mechanism includes a bailout drive gear, and wherein each of the plurality of actuation assemblies includes a gear that is selectively movable into engagement with the bailout drive gear such that rotation of the bailout drive gear can simultaneously drive at least two of the plurality of actuation assemblies.

5. The tool of claim 4, wherein each of the plurality of actuation assemblies is coupled to a switch disposed on the housing and configured to move the gear of the actuation assembly into engagement with the bailout drive gear.

6. The tool of claim 5, wherein each switch is configured to simultaneously move a corresponding motor-driven drive gear into a position in which the motor-driven drive gear is prevented from engaging with an external motor.

7. The surgical system of claim 1, wherein the bailout mechanism is configured to be manually rotated to manually drive the at least two actuation assemblies.

8. The surgical system of claim 1, wherein the bailout mechanism includes a drive recess configured to receive a drive tool.

9. The surgical system of claim 8, wherein the drive tool includes a ratchet.

10. The surgical system of claim 1, further comprising at least one indicator connected to at least one of the plurality of actuation assemblies and configured to indicate when the corresponding actuation assembly has failed.

11. The surgical system of claim 1, further comprising a plurality of bailout switches, each coupled to a corresponding actuation assembly, each bailout switch being configured to cause the corresponding actuation assembly to move into engagement with the bailout mechanism.

12. The surgical tool of claim 1, wherein the housing is configured to couple to a plurality of motors on a tool driver of a surgical system.

13. A surgical bailout method, comprising:
selectively actuating a plurality of motors in a tool driver of a robotic arm to selectively drive a plurality of drive gears disposed within a housing of a surgical tool, each of the plurality of drive gears driving an actuation assembly extending through an elongate shaft of the surgical tool to thereby actuate a function of an end effector of the tool; and
actuating a bailout assembly to simultaneously counter rotate at least two of the plurality of actuation assemblies to reverse the corresponding functions of the end effector.

14. The method of claim 13, further comprising, prior to actuating the bailout assembly, decoupling the drive gears of the at least two of the plurality of actuation assemblies from the corresponding motors.

15. The method of claim 14, wherein, simultaneously with decoupling, the at least two of the plurality of actuation assemblies moves into engagement with the bailout assembly.

16. The method of claim 14, wherein decoupling the drive gears of the at least two of the plurality of actuation assemblies from the corresponding motors comprises actuating a switch to move a coupling on a shaft having the drive gear mounted thereon away from and out of engagement with the motor.

17. The method of claim 13, wherein actuating the bailout assembly comprises rotating a tool coupled to the bailout assembly to counter rotate the at least two of the plurality of actuation assemblies.

18. The method of claim 13, wherein actuating the bailout assembly causes a bailout gear to rotate, which in turn causes a gear on each of the at least two of the plurality of actuation assemblies to rotate.

19. The method of claim 13, wherein the tool includes a plurality of indicators and each indicator indicating when an actuation assembly coupled thereto has failed.

* * * * *